United States Patent
Comelli et al.

(10) Patent No.: US 10,857,522 B2
(45) Date of Patent: Dec. 8, 2020

(54) CATALYTIC PROCESS FOR THE PRODUCTION OF PROPYLENE GLYCOL FROM GLYCEROL, A COPPER AND CERIUM CATALYST, AND A PROCESS TO PRODUCE SUCH CATALYST

(71) Applicants: CONSEJO NACIONAL DE INVESTIGACIONES CIENTIFICAS Y TECNICAS (CONICET), Buenos Aires (AR); UNIVERSIDAD NACIONAL DEL LITORAL, Prov. de Santa Fe (AR); INIS BIOTECH LLC, Kent County, DE (US)

(72) Inventors: Raul Alberto Comelli, Prov. de Santa Fe (AR); Lisandro Roberto Ferrari, Prov. de Santa Fe (AR)

(73) Assignees: CONSEJO NACIONAL DE INVESTIGACIONES CIENTIFICAS Y TECNICAS (CONICET), Buenos Aires (AR); UNIVERSIDAD NACIONAL DEL LITORAL, Santa Fe (AR); INIS BIOTECH LLC., Milford, DE (US)

( * ) Notice: Subject to any disclaimer, the term of this patent is extended or adjusted under 35 U.S.C. 154(b) by 0 days.

(21) Appl. No.: 15/537,265

(22) PCT Filed: Dec. 16, 2015

(86) PCT No.: PCT/IB2015/059673
§ 371 (c)(1),
(2) Date: Jun. 16, 2017

(87) PCT Pub. No.: WO2016/098013
PCT Pub. Date: Jun. 23, 2016

(65) Prior Publication Data
US 2017/0354957 A1   Dec. 14, 2017

(30) Foreign Application Priority Data
Dec. 17, 2014   (AR) .......................... P20140104696

(51) Int. Cl.
*B01J 23/10*   (2006.01)
*B01J 23/83*   (2006.01)
(Continued)

(52) U.S. Cl.
CPC ............. *B01J 23/83* (2013.01); *B01J 23/002* (2013.01); *B01J 35/002* (2013.01); *B01J 35/023* (2013.01);
(Continued)

(58) Field of Classification Search
CPC ........ B01J 23/83; B01J 35/002; B01J 37/088; B01J 23/002; B01J 37/0207; B01J 35/023; B01J 37/0205; B01J 2523/00; C07C 29/60
(Continued)

(56) References Cited

U.S. PATENT DOCUMENTS

2003/0098259 A1   5/2003   Kelkar et al.
2009/0156866 A1   6/2009   Cui et al.

FOREIGN PATENT DOCUMENTS

CN       102924233 A   *   2/2013
WO       WO 02/26619       4/2002
WO       WO 2006/093802    9/2006

OTHER PUBLICATIONS

Yu et al. "Aqueous hydrogenolysis of glycerol over Ni—Ce/Ac catalyst: Promoting effect of Ce on catalytic performance" Applied Catalysis A: General vol. 383, Issues 1-2, Jul. 31, 2010, pp. 73-78 (Year: 2010).*

(Continued)

*Primary Examiner* — Haytham Soliman
(74) *Attorney, Agent, or Firm* — Nixon & Vanderhye

(57) ABSTRACT

A process for producing propylene glycol from glycerol including a catalyst of Cu and Ce at concentrations of up to 15% of each metal. In addition, it is described a catalyst of Cu and Ce to perform the selective reduction of glycerol and the process of production of such catalyst.

10 Claims, 8 Drawing Sheets

(51) Int. Cl.
*B01J 37/02* (2006.01)
*C07C 29/60* (2006.01)
*B01J 35/02* (2006.01)
*B01J 37/08* (2006.01)
*B01J 35/00* (2006.01)
*B01J 23/00* (2006.01)

(52) U.S. Cl.
CPC ....... *B01J 37/0205* (2013.01); *B01J 37/0207* (2013.01); *B01J 37/088* (2013.01); *C07C 29/60* (2013.01); *B01J 2523/00* (2013.01)

(58) Field of Classification Search
USPC .......................................................... 502/304
See application file for complete search history.

(56) References Cited

OTHER PUBLICATIONS

Gandarias et al. "Liquid-phase glycerol hydrogenolysis by formic acid over Ni—Cu/Al2O3 catalysts" Journal of Catalysis vol. 290, Jun. 2012, pp. 79-89 (Year: 2012).*
Machine Translation of CN102924233 (Year: 2013).*
International Search Report, PCT/IB2015/059673, dated May 9, 2016.

* cited by examiner

CATALYTIC PROCESS FOR THE PRODUCTION OF PROPYLENE GLYCOL FROM GLYCEROL, A COPPER AND CERIUM CATALYST, AND A PROCESS TO PRODUCE SUCH CATALYST

FIELD OF THE TECHNOLOGY

This invention is intended to obtain a product from glycerol having advantages in relation to the status of the art, since it describes a process of selective reduction of glycerol to produce propylene glycol, the catalyst to carry out such process and a process to produce such catalyst, which uses low metal concentration, low reaction temperature and low pressure.

STATE OF THE ART

The process of selective reduction of glycerol to glycols is a new process driven by the growth in the supply of glycerol related to the increased production of biodiesel.

The methods of obtaining propane-1,2-diol, also called propylene glycol, from glycerol are known in the status of the art, being the selective reduction of glycerol the preferred method, wherein the variants can occur in the physical conditions of operation, such as temperature, pressure, time, among others; and also on the catalyst used.

US application US20090156866 A1 discloses a method for producing propylene glycol from glycerol using a mixed catalyst of $CuO$—$CeO_2$—$SiO_2$, in fixed bed reactor, at a temperature ranging from 170° C. to 200° C. and at a pressure ranging from 1 to 5 MPa, being the loads of the metals of the catalyst CuO (32%)—$CeO_2$ (8%)—$SiO_2$ (60%).

International application WO2014/125416 A1 describes an integrated process to prepare useful compounds, such as fuel components, wherein on one stage glycerin is turned into propylene glycol, using a copper chromite catalyst at a temperature of 250° C.

German Application DE4302464 describes the preparation of propylene glycol by ongoing hydrogenation, in liquid or gas phase, using glycerin as raw material. The catalysts used in the invention contain copper at a concentration that ranges from 30 to 40% in weight, chromium 23 to 30% and 1.5 to 3% barium.

Other applications, such as EP2565175A1, US2010312024A1, among others, use catalysts made up of high metal levels, especially noble ones, such as platinum, making the product more expensive, and also of metals that are toxic, such as chromium.

This invention solves the above problem through a catalyst that does not have noble metals for obtaining propylene glycol from glycerol, using a liquid or gaseous process, at low temperatures and low pressure, and including a bimetallic catalyst comprising low metal concentrations in order to reduce the cost and to turn it into an environmentally friendly product, without reducing neither the conversion percentage to propylene glycol, nor selectivity.

BRIEF DESCRIPTION OF THE INVENTION

This invention describes a catalytic process to produce propylene glycol from glycerol, comprising the selective reduction of such glycerol through a catalyst of copper and cerium supported on alumina, wherein the concentration of Cu is of up to 15% in weight, the concentration of Ce is of up to 15% in weight, and the operating conditions of such process include a temperature ranging from 170 to 200° C., a total pressure of 1 atmosphere, partial pressure of $H_2$ ranging from 0.3 to 1 atmosphere, a helium/hydrogen relation ranging from 0 to 3/2, a glycerol concentration ranging from 20 to 50% in weight, a liquid hourly space velocity ranging from 0.05 to 15.00 h-1, and a contact time ranging from 0.03 to 5.00 minutes.

Furthermore, this invention includes a catalyst for such catalytic process comprising copper and cerium supported on alumina wherein the concentration of Cu is of up to 15% in weight, the concentration of Ce is of up to 15% in weight; preferably such concentration of Cu is of up to 7% in weight and such concentration of Ce is of up to 7% in weight.

Another object of this invention is a process to produce the cerium and copper catalyst comprising: an alumina support with a specific surface ranging from 150 to 250 m2 g-1 and pore volume ranging from 0.1 to 1.0 cm3 g-1; copper and cerium precursors; and also comprising the following steps:

a. grinding alumina support and sieving at a particle size ranging from 35 to 80 mesh;

b. conditioning alumina particles at 110° C. for one hour and then burn them in air stream at 500° C. for 3 hours;

c. adding drop by drop the solution of the precursor of the first metal on the support until dampening the whole mass, with ongoing stirring, until the wet particles remain united despite stirring; then continuing adding 5% more of solution than the equivalent to the volume of pores corresponding to the support;

d. maintaining the impregnated support in a desiccator between 4 and 6 hours;

e. drying in oven at 110° C. for at least 8 hours;

f. burning the dried impregnated support in air stream at temperatures of up to 300° C. for at least 1.5 hours, leaving the metal oxide on the support;

g. cooling in air stream of nitrogen;

h. adding drop by drop the solution of the precursor of the second metal on the support until damping the whole mass, with ongoing stirring, until wet particles remain united although stirring; then, continuing adding 5% more of solution than the equivalent to the volume of the pores belonging to the support;
i. maintaining the impregnated support in desiccator between 4 and 6 hours;
j. drying in oven at 110° C. for at least 8 hours;
k. burning the dry impregnated support in air stream at a temperature of up to 300° C. for at least 1.5 hours, leaving the metal oxide on the support;
l. cooling in a stream of nitrogen.

Wherein in such step c), such first metal is copper; and on the second impregnation of such step h), such second metal is cerium. Alternatively, such first metal of step c) is cerium and such second metal of step h) is copper.

Wherein from such production process, it is obtained a catalyst comprising a concentration of cerium of up to 15% in weight and a concentration of copper of up to 15% in weight; preferably, it comprises a concentration of cerium of up to 7% in weight and a concentration of copper of up to 7% in weight

DETAILED DESCRIPTION OF THE INVENTION

1. Preparation of the Catalysts

The base material used for preparations was commercial gamma alumina (identified as $\gamma$-$Al_2O_3$, with specific surface of 199 $m^2$ $g^{-1}$ and pore volume of 0.5 $cm^3$ $g^{-1}$), which was ground and sieved at particle size of 35-80 mesh, conditioned at 110° C. for one hour in oven and then burned in air stream at 500° C. for 3 hours.

The precursors of copper (Cu) and cerium (Ce) used were hexahydrate copper nitrate and hexahydrate cerium nitrate, respectively. The concentrations of the common impregnation solutions used were 45.5 and 9.1 g/l of Cu and Ce, respectively, modifying them to obtain other metal loadings.

Impregnation of metal precursors on the support was carried out by means of the technique of incipient wetness impregnation. It was added drop by drop the solution of the desired precursor on the support until damping the whole mass, with ongoing stirring, until the wet particles remain united despite stirring; then, it was added 5% more of solution than the equivalent to the volume of pores corresponding to the support. The impregnated material was kept 4-6 hours in a desiccator to allow proper interaction between the support and the solution of the metal precursor; then, it was taken to oven at 110° C. all the night. The impregnated and dried material was burned in a tubular reactor with fixed bed and downstream flow, heated by an electric oven, passing through the catalyst's bed an air stream of 50 $cm^3$/min., with a heating rate from 4.5° C./min to 300° C. and maintaining such temperature for 2.5 hours to achieve decomposition of the precursor, thus remaining the metal oxide on the support; after burning, the material was cooled in a nitrogen stream. To introduce the second metal precursor the above sequence is repeated from the step implying addition drop by drop of the solution with the new precursor. Monometallic materials prepared were identified as Cu/$\gamma$-$Al_2O_3$ and Ce/$\gamma$-$Al_2O_3$, while bimetallic ones: when entering first Cu and then Ce as Cu—Ce/$\gamma$-$Al_2O_3$ and when the order is reversed, that is Ce is impregnated in first place and then Cu, as Ce—Cu/$\gamma$-$Al_2O_3$.

2. Pretreatment of Catalysts

The pretreatment steps were: i) burning, by passing through the material bed an air stream of 50-100 $cm^3$ $min^{-1}$, with a heating rate of 3-6° C. $min^{-1}$ up to the selected temperature and maintaining it for 2-4 hours; ii) cooling, up to room temperature in nitrogen stream; and iii) reduction, in hydrogen flow of 50-100 $cm^3$ $min^{-1}$, using the same heating rate than for burning, and maintaining it for 1-3 hours at 250-400° C.

For bimetallic catalysts, prepared by following different sequences of impregnation of precursor, that is, in first place Cu and then Ce or in first place Ce and then Cu, the pretreatment conditions were selected according to the precursors used, including a burning step between impregnations and a single reduction step. Such pretreatment reduction step comprises hydrogen flow of 70 $cm^3$/min, using a heating rate from 4.5° C./min to 300° C. and maintaining such temperature for 2 hours to obtain in the material the corresponding metal sites.

Table 1 shows details of the identification of catalysts, as well as the sequence of impregnation of metals, the loads and burning and reduction pretreatment steps.

TABLE 1

Identification of catalysts, sequence of addition of metals, loads thereof and burning and reduction steps.

| | Impregnation 1 | | Pretreatments | | Impregnation 2 | | Pretreatments | |
|---|---|---|---|---|---|---|---|---|
| ID | Metal | Load (%) | Burning | Reduction | Metal | Load (%) | Burning | Reduction |
| Cu/$\gamma$-$Al_2O_3$ | Cu | 4-15 | Yes | Yes | — | — | — | — |
| Ce/$\gamma$-$Al_2O_3$ | Ce | 4-12 | Yes | Yes | — | — | — | — |
| Cu—Ce/$\gamma$-$Al_2O_3$ | Cu | 4-15 | Yes | No | Ce | 4-12 | Yes | Yes |
| Ce—Cu/$\gamma$-$Al_2O_3$ | Ce | 4-12 | Yes | No | Cu | 4-15 | Yes | Yes |

3. Catalytic Assessment

The ranges of operating conditions used to assess the behavior of materials were:

Reaction temperature: 170-230° C.
Total pressure: 1 atm
Hydrogen partial pressure: 0.3-1 atm
Helium/hydrogen relation: 0-1.5
Glycerol concentration in supply solution: 20-50% (w/v)
Liquid hourly space velocity (LHSV, in relation to glycerol): 0.05-15.00 $h^{-1}$
Contact time ($\theta_c$, in relation to hydrogen): 0.03-5.00 min

EXAMPLES

Examples 1-3

Figure 1:
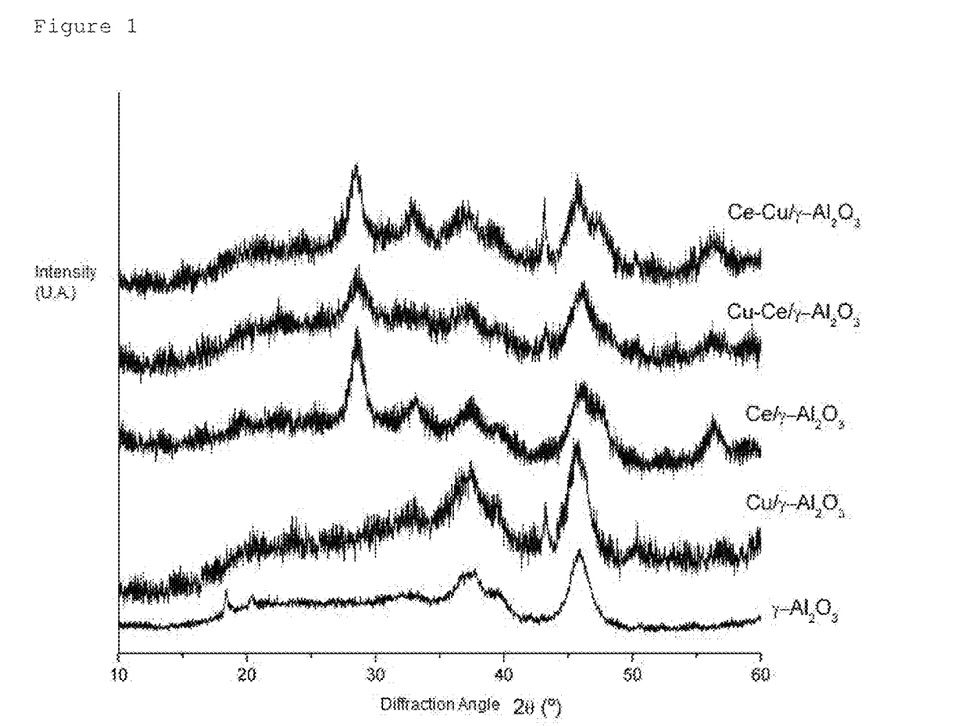
FIG. 1: XRD patterns corresponding to alumina and to catalysts made up of Cu—Ce impregnated on alumina.
Figure 2:
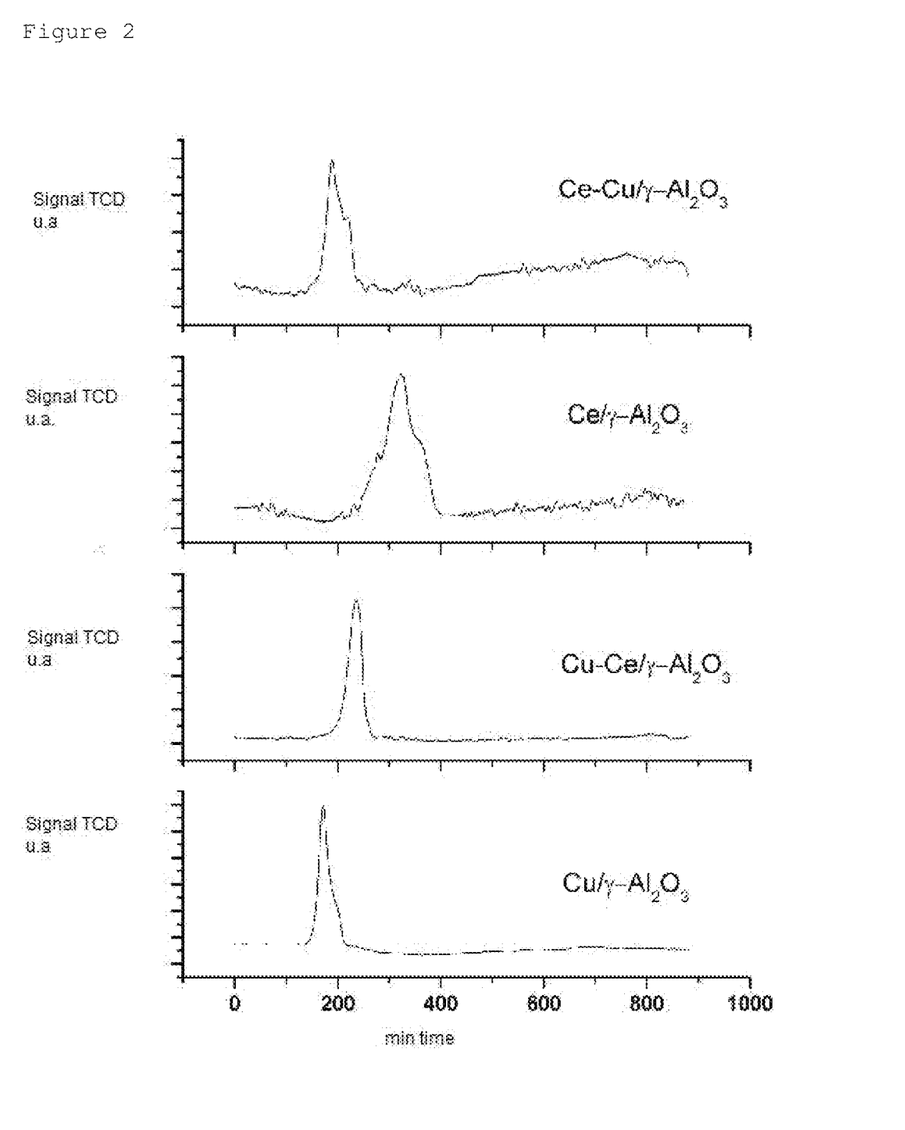
FIG. 2: RTP profiles of catalysts made up of Cu—Ce impregnated on alumina.
Figure 3:
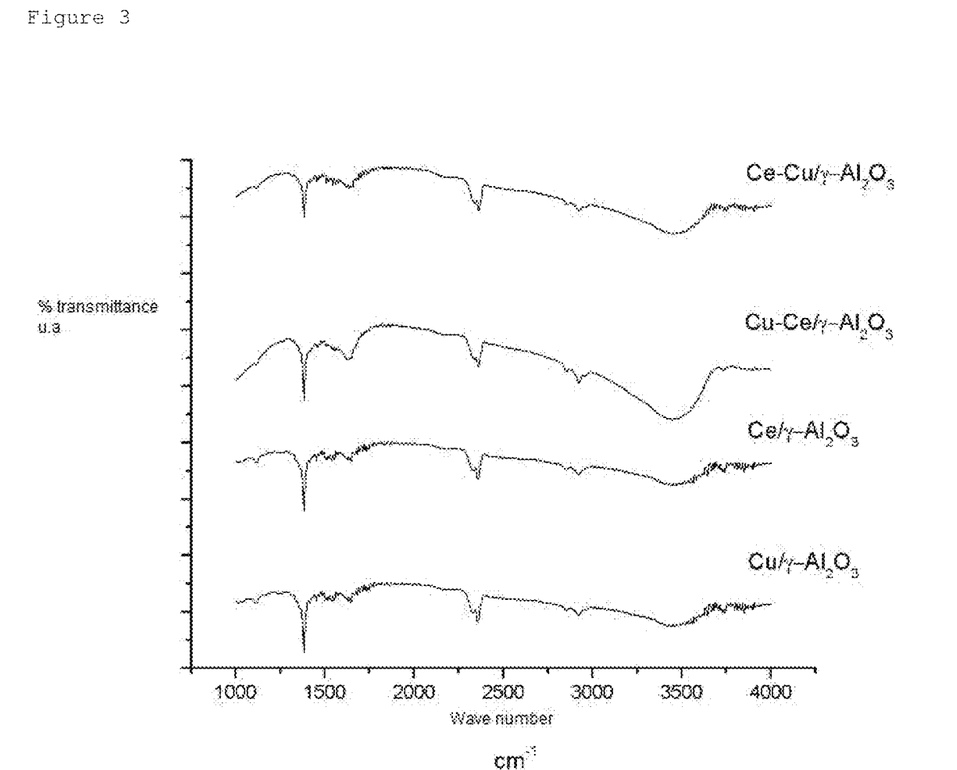
FIG. 3: FTIR spectra of the catalysts made up of Cu—Ce impregnated on alumina.

FIGS. 1-2-3 show characterizations by XRD, TPR and FTIR, respectively, for monometallic catalysts of Cu and Ce and bimetallic ones of Cu—Ce and Ce—Cu prepared as detailed herein.

FIG. 1 shows the characterization by X-ray diffraction (XRD) of gamma alumina ($\gamma$-$Al_2O_3$) and catalysts of copper (Cu) and cerium (Ce) impregnated on γ-Al$_2$O$_3$. γ-Al$_2$O$_3$ has its typical pattern. Cu impregnated on γ-Al$_2$O$_3$ (Cu/γ-Al$_2$O$_3$) shows a sharp peak at 43°, corresponding to Cu metal species of Cu, without changing the crystal structure of γ-Al$_2$O$_3$. Impregnation of Ce on γ-Al$_2$O$_3$ (Ce/γ-Al$_2$O$_3$) causes peaks, one at 28 and the other one at 56°, respectively, corresponding to metal species of Ce, without changing the crystal structure of γ-Al$_2$O$_3$. By impregnating Cu and then Ce (Cu—Ce/γ-Al$_2$O$_3$), the peak intensity of 43° is lower and peaks at 28 and 56° appear; by impregnating in reverse order, that is, in first place Ce and then Cu (Ce—Cu/γ-Al$_2$O$_3$), the peak of 43° is more intense and sharp, which is related to the dispersion of Cu species.

FIG. 2 shows the characterization by temperature programmed reduction (TPR) of γ-Al2O3 and catalysts of Cu and/or Ce impregnated on γ-Al2O3. γ-Al2O3 (profile not shown) does not show hydrogen consumption. Cu/γ-Al2O3 profile shows that the reduction of species begins at 170° C., with a main max. peak at 225° C. and a small shoulder between 250 and 277° C. Ce/γ-Al2O3 has a wider and offset reduction profile at higher temperature; impregnated species on the support start to reduce at 250° C., with main max. peak at 350° C. and a small shoulder between 377 and 425° C. For Cu—Ce/γ-Al2O3, the reduction peak remains well defined but it shifts to higher temperature, being the main max. peak at 265° C. For Ce—Cu/γ-Al2O3, the species start to reduce at 165° C., being the main max. peak at 220° C. and a second small peak mounted on the tail of the main one, with max. peak at 250° C.

FIG. 3 shows the characterization by Fourier transform infrared spectroscopy (FTIR) of γ-Al$_2$O$_3$ and catalysts of Cu and/or Ce impregnated on γ-Al$_2$O$_3$. All spectra are similar and they include in the high-frequency region an intense band centered at 3500 cm$^{-1}$, characteristic of γ-Al$_2$O$_3$, related to OH interaction of the support and/or chemisorbed water to the support, and a weak band at 3780 cm$^{-1}$, related to acid, neutral and basic OH groups. In the low-frequency region, both monometallic catalysts (Cu/γ-Al$_2$O$_3$ and Ce/γ-Al$_2$O$_3$) show a well-defined sharp band at 1385 cm$^{-1}$, which also appears on bimetallic ones, regardless of the order of impregnation.

Examples 4-9

The behavior of six catalysts containing Cu was assessed during hydrogenolysis reaction or selective reduction of glycerol to propylene glycol.

The catalysts were:
Cu/H-FER: material prepared and impregnated by incipient wetness Cu on the acid form of ferrierite zeolite, which has a porous structure that allows housing the glycerol molecule. The Cu load was 6.6%.
Cu/K-FER: material prepared and impregnated by incipient wetness Cu on the potassium form of zeolite ferrierite. Cu loading was 6%.
Cu Chromite: Commercial material (Sud Chemie).
Cu/γ-Al$_2$O$_3$: material prepared according to the technique herein described. The load of Cu was 6.6%.
Cu—Ce/γ-Al$_2$O$_3$: material prepared according to the technique herein described. The loads of Cu and Ce were 6.6 and 6.0%, respectively.
Ce—Cu/γ-Al$_2$O$_3$: material prepared according to the technique herein described. The loads of Ce and Cu were 6.0 and 6.6% respectively.

The operating conditions for catalytic assessment were: 200° C., atmospheric pressure, hydrogen partial pressure of 1 atm, glycerol concentration in supply solution of 20% in weight, $θ_c$ 0.64 min, and LHSV 0.40 h$^{-1}$.

Figure 4:
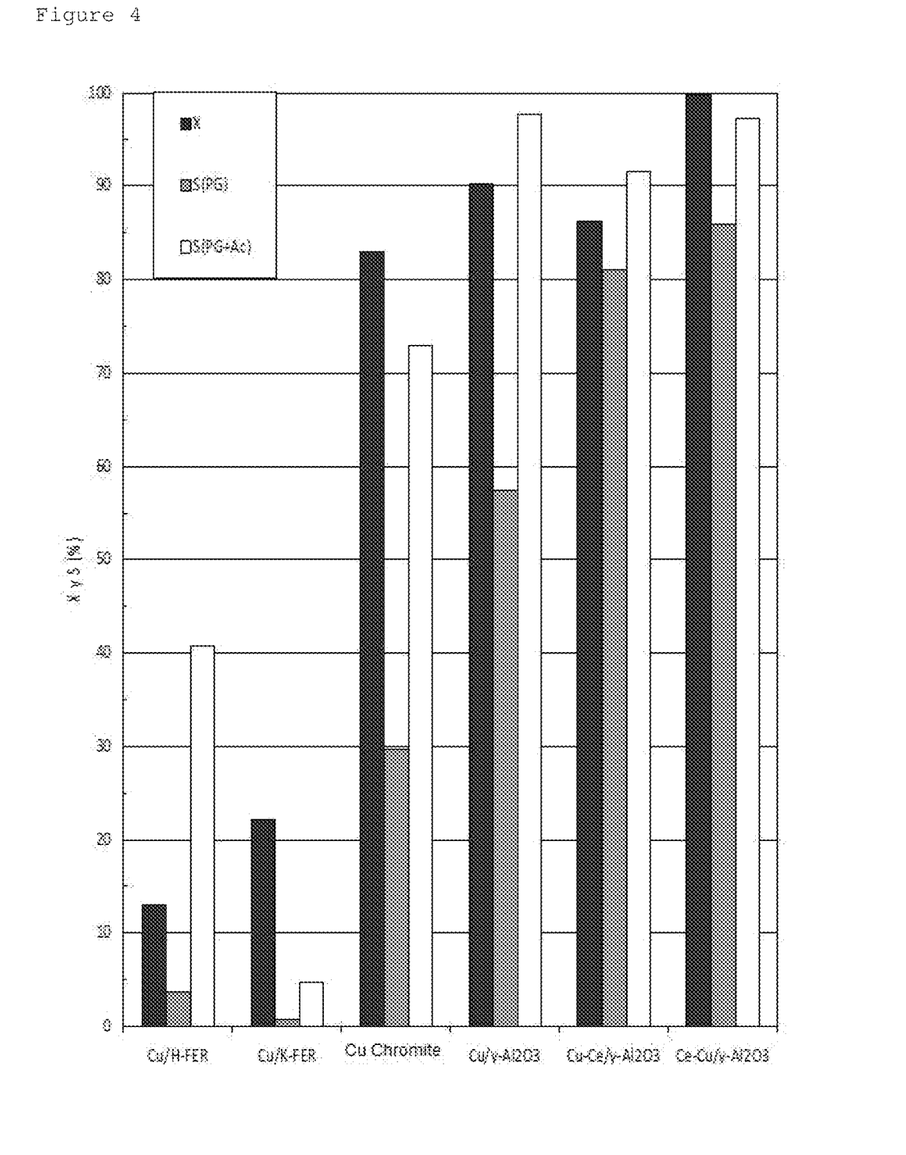
FIG. 4: Conversion of glycerol (X) and selectivities to propylene glycol ($S_{PG}$) and propylene glycol plus acetol ($S_{PG+AC}$) for different Cu catalysts.

FIG. 4 compares the catalytic behavior, stated as glycerol conversion (X) and selectivities to propylene glycol (S$_{PG}$) and propylene glycol plus acetol (S$_{PG+AC}$) for the different catalysts with Cu. Acetol, intermediate reaction product (obtained in the first dehydration step and then hydrogenated to propylene glycol), can be turned into propylene glycol, so selectivity to propylene glycos plus acetol is shown, thus allowing the comparison of materials and getting an idea of other undesirable byproducts. Bimetallic catalysts of Cu and Ce achieve the best catalytic performance, being slightly better the one impregnated in first place with Ce and then with Cu.

Examples 10-14

Catalysts Cu—Ce/γ-Al$_2$O$_3$ impregnated with loads of 6.6% of Cu and 6% of Ce were assessed with respect of the reaction of selective reduction of glycerol to propylene glycol.

The operating conditions used for the catalytic assessment were: 200° C., atmospheric pressure, glycerol concentration in supply solution 20% in weight and LHSV 0.40 h$^{-1}$, $θ_c$ varied between 0.64 and 1.50 min.

Table 2 shows the operating conditions modified in Examples 10-14 and identification of each one.

TABLE 2

Operating conditions modified in examples 10-14 and identification of each one.

Figure 5:
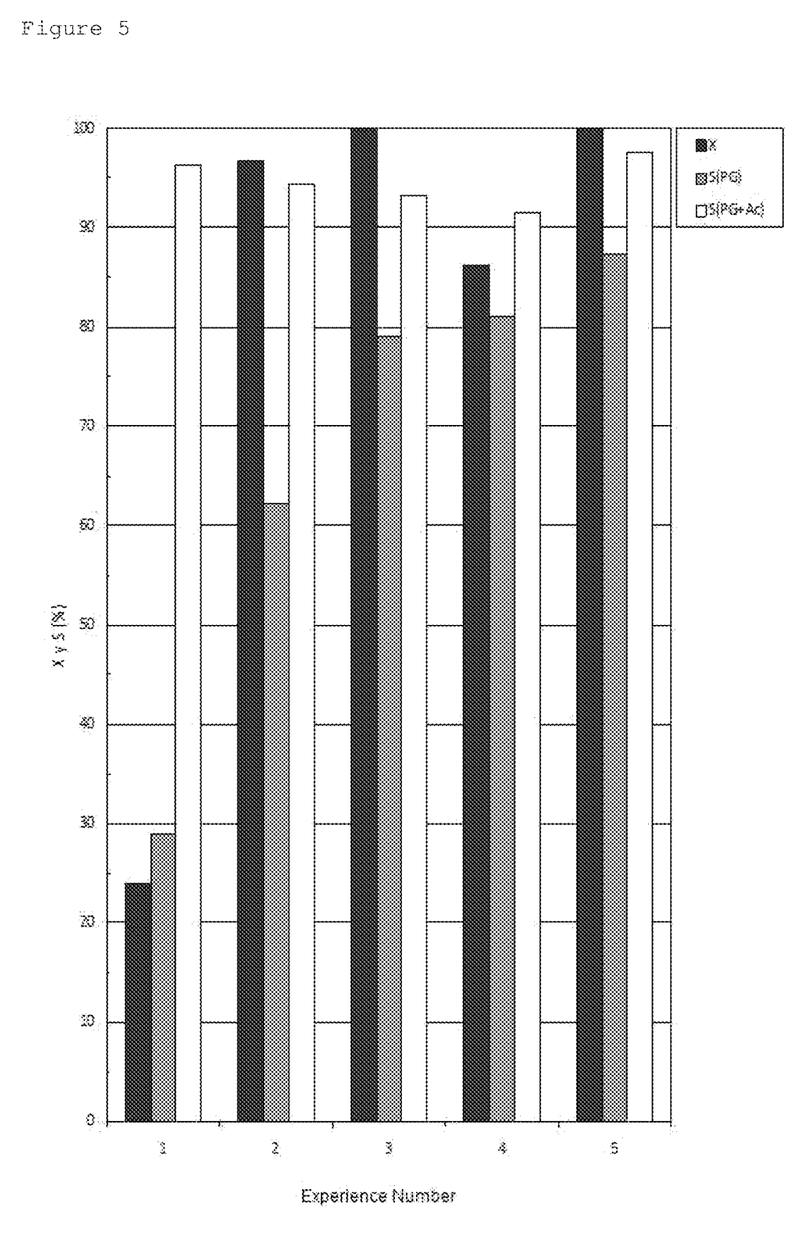
FIG. 5: Conversion of glycerol (X) and selectivities to propylene glycol ($S_{PG}$) and propylene glycol plus acetol ($S_{PG+AC}$) for different catalysts of Cu—Ce/$Al_2O_3$-experience conditions table 2.

| Example | Prereduction | $θ_c$ (min) | Relation He/H$_2$ | Identification in FIG. 5 |
| --- | --- | --- | --- | --- |
| 10 | No | 0.64 | 0 | Experience 1 |
| 11 | Yes | 1.50 | 1.33 | Experience 2 |
| 12 | Yes | 0.82 | 0.27 | Experience 3 |
| 13 | Yes | 0.64 | 0 | Experience 4 |
| 14 | Yes | From 0.82 to 0.64 | From 0.27 to 0 | Experience 5 |

FIG. 5 compares the catalytic behavior, considering conversion of glycerol (X) and selectivities to propylene glycol (S$_{PG}$) and propylene glycol plus acetol (S$_{PG+AC}$) for the different examples. Example 10 shows the importance and need of prereduction to reaction. Examples 11 to 14 show that an increased flow of H$_2$ favors selectivity to propylene glycol and that a strategy of co-supply with inert may result in an additional improvement of selectivity.

Examples 15-18

Catalysts Ce—Cu/γ-Al$_2$O$_3$, impregnated with loads of 6% of Ce and 6.6% and 12% of Cu, were assessed in the selective reduction of glycerol to propylene glycol.

The operating conditions used for catalytic assessment were: 200° C., atmospheric pressure, glycerol concentration in supply solution 20% in weight and LHSV 0.4 h$^{-1}$, $θ_c$ varied between 0.64 and 1.50 min.

Table 3 shows the operating conditions modified in Examples 15-18 and the identification of each one.

TABLE 3

Operating conditions modified in examples 15-18 and identification of each one.

Figure 6:
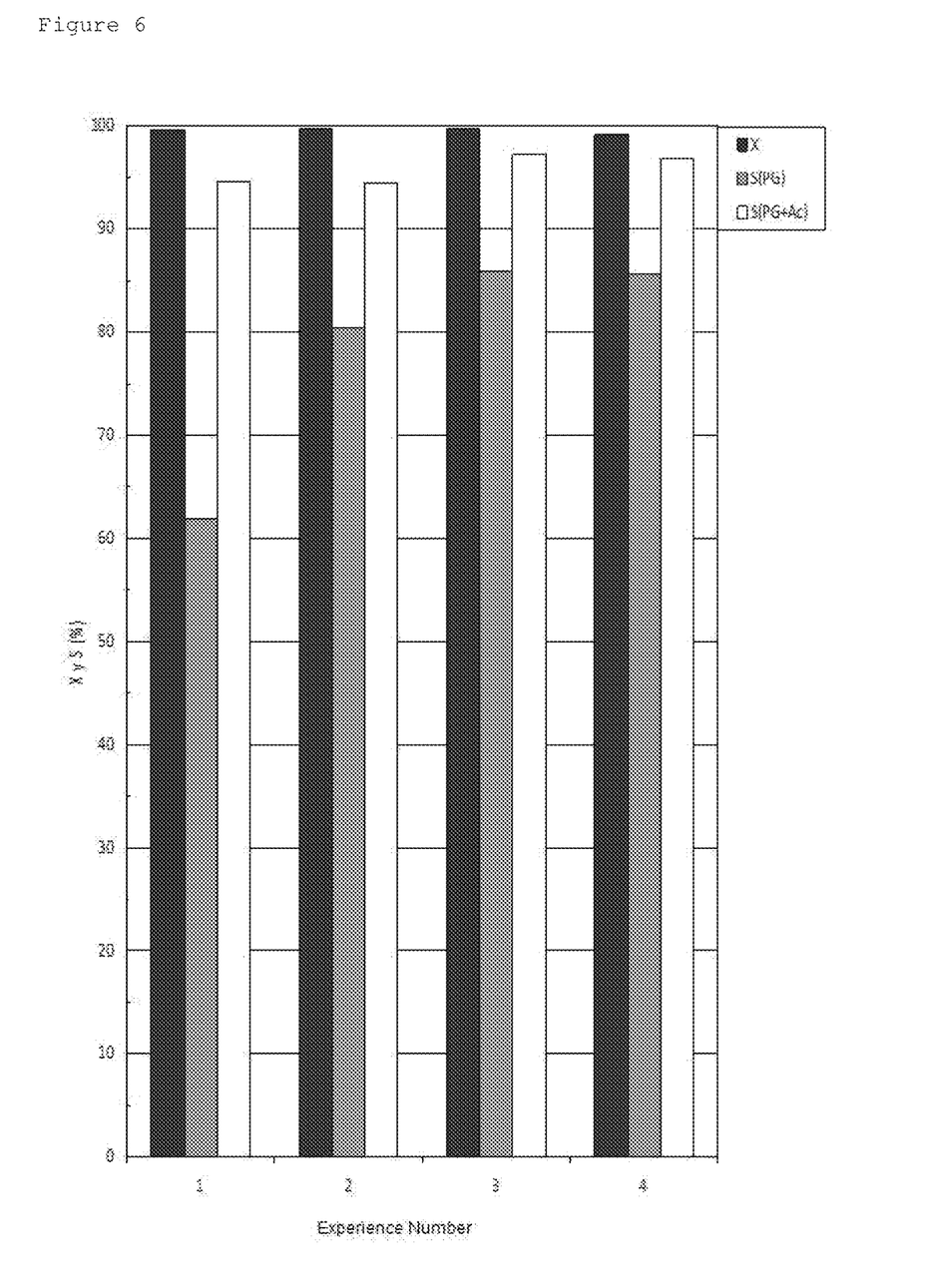
FIG. 6: Conversion of glycerol (X) and selectivities to propylene glycol ($S_{PG}$) and propylene glycol plus acetol ($S_{PG+AC}$) for different catalysts of Ce—Cu/$Al_2O_3$— experience conditions table 3.

| Example | Load of Cu (%) | $\theta_c$ (min) | Relation He/H$_2$ | Identification in FIG. 6 |
|---|---|---|---|---|
| 15 | 6.6 | 1.50 | 1.33 | Experience 1 |
| 16 | 6.6 | 0.82 | 0.27 | Experience 2 |
| 17 | 6.6 | 0.64 | 0 | Experience 3 |
| 18 | 12.0 | 0.82 | 0.27 | Experience 4 |

FIG. 6 compares the catalytic behavior, considering conversion of glycerol (X) and selectivities to propylene glycol ($S_{PG}$) and to propylene glycol plus acetol ($S_{PG+AC}$) for the different examples. Glycerol conversion is completed with these catalysts, increasing the selectivity to propylene glycol by increasing the flow of hydrogen. Twice the increase of the load of Cu does not result in increased activity of the material.

Examples 13 and 17

Figure 7:
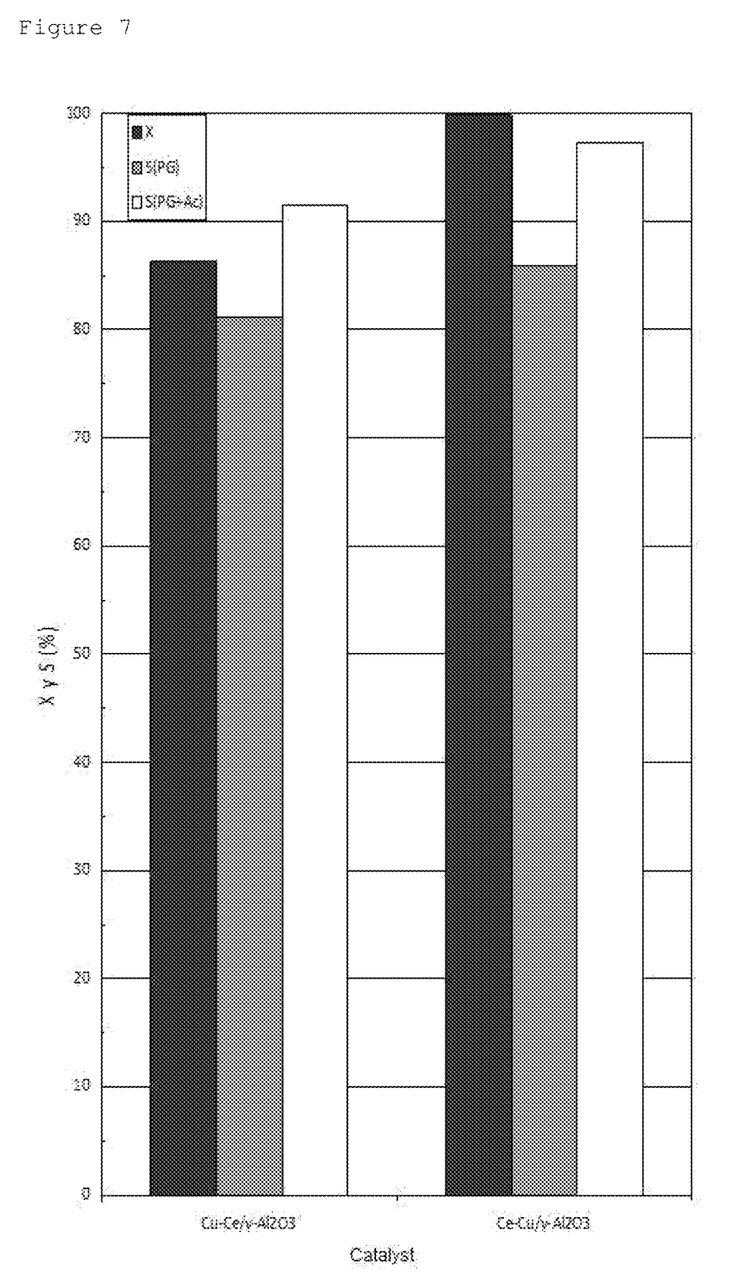
FIG. 7: Comparison of conversion of glycerol (X) and selectivities to propylene glycol ($S_{PG}$) and propylene glycol plus acetol ($S_{PG+AC}$) for Cu—Ce/$Al_2O_3$ and Ce—Cu/$Al_2O_3$.

FIG. 7 compares the catalytic behavior of Cu—Ce/γ-Al$_2$O$_3$ (Example 13) with Ce—Cu/γ-Al$_2$O$_3$ (Example 17), considering conversion of glycerol (X) and selectivities to propylene glycol ($S_{PG}$) and to propylene glycol plus acetol ($S_{PG+AC}$) under similar reaction conditions. The operating conditions used were: 200° C., atmospheric pressure, glycerol concentration in supply solution 20% in weight, $\theta_c$ 0.64 min and LHSV 0.40 h$^{-1}$.

The sequence of impregnation is important; adding in first place Ce and then impregnation of Cu leads to a material that reaches full conversion of glycerol, as well as higher selectivity to PG and lower quantity of byproducts (difference between 100 and selectivity to PG plus acetol).

Examples 19-23

Catalysts Ce—Cu/γ-Al$_2$O$_3$, impregnated with loads of 6% of Ce and 6.6 of Cu, showing better performance in the selective reduction of glycerol to propylene glycol were assessed by changing reaction conditions.

The operating conditions that were held steady for catalytic assessment were: 200° C., atmospheric pressure (hydrogen only), varying the catalyst mass, the flow of hydrogen and the glycerol concentration in the supply solution (20-50% in weight).

Table 4 shows the operating conditions modified in Examples 19-23 and the identification of each one.

TABLE 4

Operating conditions modified in examples 19-23 and the identification of each one.

Figure 8:
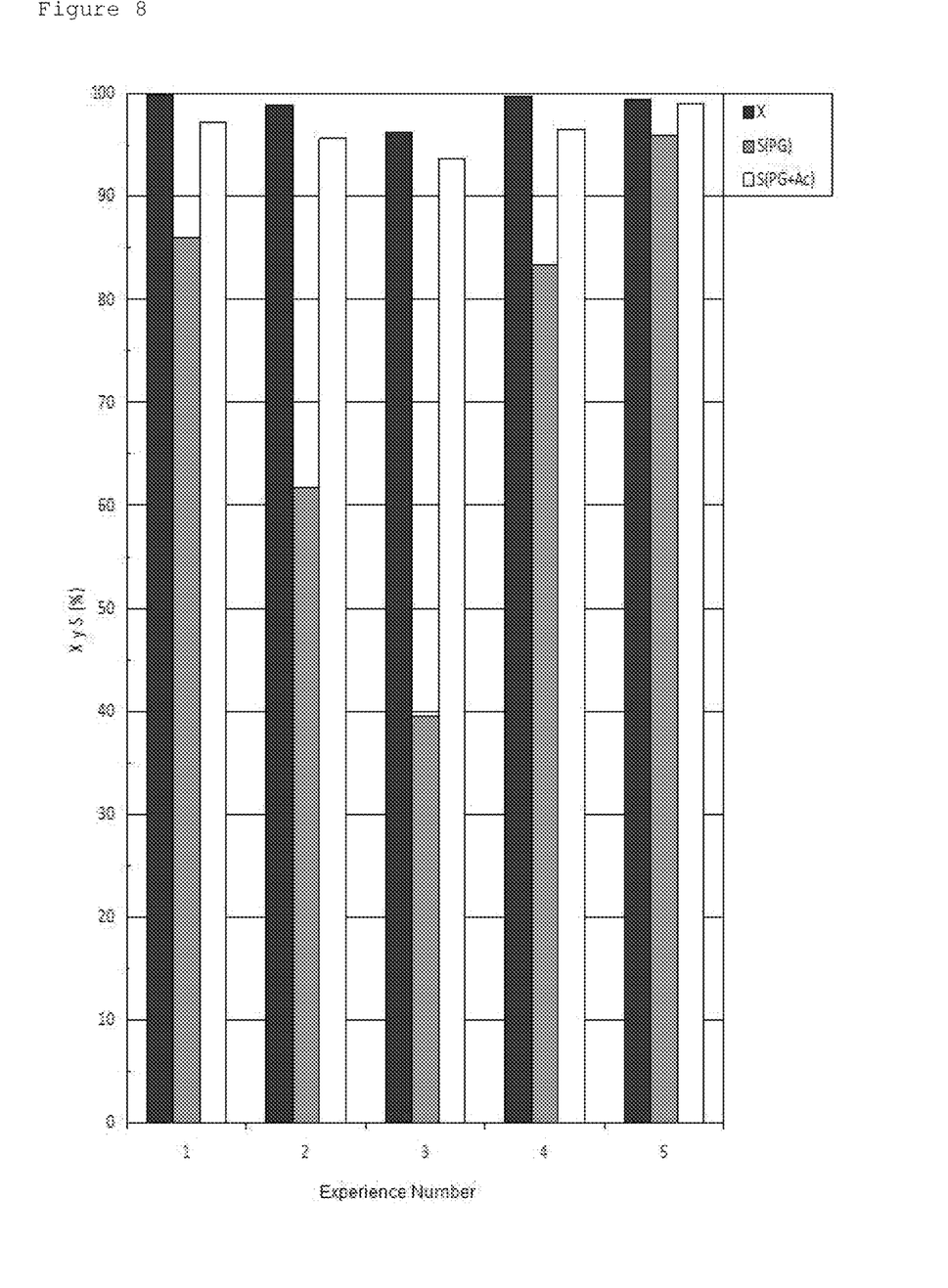
FIG. 8: Conversion of glycerol (X) and selectivities to propylene glycol ($S_{PG}$) and propylene glycol plus acetol ($S_{PG+AC}$) with Ce—Cu/$Al_2O_3$ catalyst—experience conditions table 4

| Example | $\theta_c$ (min) | LHSV (h$^{-1}$) | Identification in FIG. 8 |
|---|---|---|---|
| 19 | 0.64 | 0.40 | Experience 1 |
| 20 | 3.21 | 0.08 | Experience 2 |
| 21 | 3.21 | 0.20 | Experience 3 |
| 22 | 0.64 | 0.40 | Experience 4 |
| 23 | 0.13 | 0.40 | Experience 5 |

FIG. 8 compares the catalytic behavior, considering conversion of glycerol (X) and selectivities to propylene glycol ($S_{PG}$) and to propylene glycol plus acetol ($S_{PG+AC}$) for the different examples. The conversion of glycerol is higher than 96% in all cases, being affected selectivity to propylene glycol according to reaction conditions, but not the sum of propylene glycol and acetol. Therefore, by selecting the operating conditions, it can be reached 99.5% conversion, 96% selectivity to PG 96% and selectivity to propylene glycol plus acetol 99%, thus obtaining also 1% of byproducts.

Once described and established the nature of the invention and its embodiment, it is hereby claimed as follows:

1. A process for producing a catalyst; comprising the following steps:
   a. grinding an alumina support to produce alumina particles and sieving to a particle size ranging between 35 and 80 mesh;
   b. conditioning the alumina particles at 110° C. for one hour and then burning them in air stream at 500° C. for 3 hours;
   c. adding drop by drop the solution of the precursor of a first metal on the alumina particles support to damp the whole mass of alumina particles, with ongoing stirring, until wet particles remain united despite the stirring; then, continue adding 5% more solution than the equivalent to the volume of pores belonging to the support;
   d. maintaining the impregnated support in a desiccator between 4 and 6 hours;
   e. drying in oven at 110° C. for at least 8 hours;
   f. burning the dried impregnated support in air stream at a temperature of up to 3000 C for at least 1.5 hours, remaining the metal oxide on the support;
   g. cooling in a stream of nitrogen;
   h. adding drop by drop the solution of precursor of a second metal on the alumina particles support until damping the whole mass of alumina particles, with ongoing stirring, until the wet particles remain united despite the stirring; then, continue adding 5% more of solution than the equivalent to the volume of the pores belonging to the support;
   i. maintaining the impregnated support in a desiccator between 4 and 6 hours;
   j. drying in oven at 110° C. for at least 8 hours;
   k. burning the dried impregnated support in air stream at a temperature of up to 3000 C for at least 1.5 hours, remaining the metal oxide on the support; and
   l. cooling in a stream of nitrogen;
   wherein x-ray diffraction of said catalyst shows peaks at 43°, 28° and 56°.

2. The process of claim 1 wherein the first metal of step c) is copper and the second metal of step h) is cerium.

3. The process of claim 1 wherein the first metal of step c) is cerium and the second metal of step h) is copper.

4. The process of claim 1 wherein the catalyst obtained comprises a concentration of cerium of up to 15% by weight and a concentration of copper of up to 15% by weight.

5. The process of claim 1 wherein the catalyst obtained comprises a concentration of cerium of up to 7% by weight and a concentration of copper of up to 7% by weight.

6. A catalyst made by the process of claim 1 and comprising copper and cerium supported on alumina, wherein the concentration of Cu is up to 10% by weight, the concentration of Ce is up to 10% by weight.

7. The catalyst of claim 6 wherein the concentration of Cu is up to 7% by weight and the concentration of Ce is up to 7% by weight.

8. The catalyst of claim 6 comprising: an alumina support with specific surface ranging between 150 and 250 m$^2$ g$^{-1}$ and pore volume ranging between 0.1 and 1.0 $cm^3\ g^{-1}$; copper oxide; and cerium oxide.

9. A catalytic process for producing propylene glycol by the selective reduction of glycerol comprising the following steps:
   a. providing a stream of glycerol and $H_2$;
   b. contacting the stream of step with the catalyst of claim 3; and
   c. obtaining a stream of propylene glycol.

10. The catalytic process of claim 9 wherein the operating conditions of step b comprise the following: a temperature between 170 and 200° C.; a total pressure of 1 atm; a partial pressure of $H_2$ ranging between 0.3 and 1 atm; a relation of helium/hydrogen ranging between 0 and 3/2; a concentration of glycerol ranging between 20 and 50% in weight; a liquid hourly space velocity ranging between 0.05 and 15.00 $h^{-1}$; and a contact time ranging between 0.03 and 5.00 minutes.

* * * * *